(12) United States Patent
Rezai et al.

(10) Patent No.: US 10,859,490 B2
(45) Date of Patent: Dec. 8, 2020

(54) SYSTEM AND METHOD FOR PHOTO-THERMAL ANALYSIS OF IMMUNOASSAY TESTS

(71) Applicants: Pouya Rezai, Maple (CA); Nima Tabatabaei, Toronto (CA); Ashkan Ojaghi, Atlanta, GA (US)

(72) Inventors: Pouya Rezai, Maple (CA); Nima Tabatabaei, Toronto (CA); Ashkan Ojaghi, Atlanta, GA (US)

( * ) Notice: Subject to any disclaimer, the term of this patent is extended or adjusted under 35 U.S.C. 154(b) by 226 days.

(21) Appl. No.: 15/839,325

(22) Filed: Dec. 12, 2017

(65) Prior Publication Data

US 2019/0154564 A1 May 23, 2019

(30) Foreign Application Priority Data

Nov. 23, 2017 (CA) ...................................... 2986532

(51) Int. Cl.
| | |
|---|---|
| *G01N 21/71* | (2006.01) |
| *G01N 21/17* | (2006.01) |
| *G01N 33/50* | (2006.01) |
| *G01N 33/53* | (2006.01) |
| *G01N 33/558* | (2006.01) |
| *G01N 33/68* | (2006.01) |
| *G01N 33/543* | (2006.01) |
| *G03C 1/498* | (2006.01) |

(52) U.S. Cl.
CPC .......... *G01N 21/171* (2013.01); *G01N 21/71* (2013.01); *G01N 33/50* (2013.01); *G01N 33/53* (2013.01); *G01N 33/54386* (2013.01); *G01N 33/558* (2013.01); *G01N 33/6803* (2013.01); *G03C 1/4989* (2013.01); *G01N 2021/1714* (2013.01); *G01N 2800/00* (2013.01)

(58) Field of Classification Search
None
See application file for complete search history.

(56) References Cited

U.S. PATENT DOCUMENTS

| | | | | |
|---|---|---|---|---|
| 5,267,019 | A * | 11/1993 | Whittaker | ................ G01J 3/02 250/343 |
| 8,421,017 | B2 * | 4/2013 | McGill | ................ G01N 21/64 250/338.5 |
| 2005/0173637 | A1 * | 8/2005 | Abrahamson | ........ G01N 21/359 250/341.1 |
| 2013/0134310 | A1 * | 5/2013 | Furstenberg | ............. G01J 3/02 250/341.6 |
| 2014/0377770 | A1 * | 12/2014 | Bischof | ............. G01N 21/8483 435/7.1 |
| 2016/0216260 | A1 * | 7/2016 | Horning | ............... G01N 33/558 |
| 2016/0245748 | A1 * | 8/2016 | Gasperino | ............. G01N 21/63 |

* cited by examiner

*Primary Examiner* — Neil N Turk
(74) *Attorney, Agent, or Firm* — Roberts Calderon Safran & Cole P.C.; Jorie L. Stroup

(57) ABSTRACT

A system and method for photo-thermal imaging of a lateral flow immunoassay (LFA) device are provided. The system includes an intensity modulated heat source directed at a surface of the LFA device to selectively excite chromophore particles of interest and a thermal capture device configured to capture thermal waves emitted from the surface of the LFA device as a radiometric signal. A computing device, in communication with the thermal capture device, receives the radiometric signal and executes lock-in demodulation to detect surface or subsurface inhomogeneities of the LFA device.

18 Claims, 4 Drawing Sheets

SYSTEM AND METHOD FOR PHOTO-THERMAL ANALYSIS OF IMMUNOASSAY TESTS

TECHNICAL FIELD

The present invention relates generally to the field of thermal imaging, and more particularly to a system and method for using photo-thermal imaging in interpretation of lateral flow immunoassay devices.

BACKGROUND

Point-of-care diagnostic devices allow for medical diagnostic testing at or near the time and place of patient care; in contrast to testing that is wholly or mostly confined to medical laboratories. Among various available point-of-care diagnostic devices, lateral flow immunoassay (LFA) devices are particularly advantageous due to, for example, low-cost commercial viability, rapid identification of disease or biochemical conditions, ease of use with minimal user training, device portability at a physician's office or at a patient's side, and device robustness and disposability that eliminates contamination or safety hazards. LFA devices have been widely used in medical diagnostics, food and beverage manufacturing and water monitoring applications for detection of a wide variety of analytes such as hormones, toxic chemicals or pathogenic microorganisms in different fluidic specimens.

LFA devices are commercially available either in strip or cassette formats. LFA strips typically consist of four major components, as shown for example in FIG. 4: a sample pad, a conjugate pad, a reaction membrane, and a waste absorbent pad. These components are typically fixed onto a plastic backing card.

The sample pad is typically made of cellulose and glass fiber and the fluidic specimen to be tested is applied on this pad to start the assay. The sample is transported via capillary action to the conjugations pad, occasionally accompanied by modifying the sample pH, particulate content and fluidic constituents to prevent any non-specific bonding of the analytes to label particles pre-immobilized on the conjugation pad. The most widely used labels are antibody coated Gold Nano-Particles (GNPs) dry-stored onto the conjugation pads that are rehydrated and mixed with the sample as the capillary flow continues along the LFA strip. The target analytes (i.e., antigens) within the sample get immunologically captured by the antibodies on GNPs and carried along the nitrocellulose reaction membrane. This membrane contains the test and the control lines that are functionalized with antibodies against target antigens and the primary antibodies on GNPs, respectively. Continuous accumulation of GNP-antigen complexes on the test line typically leads to formation of a reddish color band that can be used for detection of target antigens in the sample. In the competitive format LFA, the absence of the color at the test line is an indication of the presence of the target antigen. The appearance of the control line ensures that the test is valid and the assay is functioning correctly. The absorbent pad, also known as the wicking pad, absorbs the sample fluid off of the membrane and ensures capillary flow in the right direction and at an appropriate flow rate.

Interpretation of LFA results is often based on visual detection of the test and control lines on the strip. Visual interpretation is often prone to human errors and can be inaccurate and subjective. The increased color intensity of the test line corresponds to the amount of target antigen in the sample that cannot be quantified with visual inspection. As such, optical scanning readers have been developed to acquire images from the LFA strips and employ accurate image analysis algorithms to measure the color intensities of test and control lines for quantitative interpretation of LFA results. However, these devices typically only rely on the reflective optical signals, mostly in the visible spectral range, from the surface of the devices to quantify the results. Consequently, a large amount of signal corresponding to the GNPs trapped inside the bulk of the membrane is lost leading to suboptimal detection limits and sensitivities in optical readers.

Several approaches have aimed to address these issues, including methods ranging from fluorescence imaging and Surface-Enhanced Raman Scattering (SERS) detection, to Resonant Coil Magnetometer (RCM) based inspection. However, the high equipment cost, relatively low speed, and complexity of these methods limit their adaptation in clinical use.

Approaches based on thermal contrast have also been used to improve the sensitivity of traditional colorimetric (i.e., gold nanoparticle based) LFAs, using GNP surface plasmon resonance under laser irradiation. However, such approaches typically suffer from low readout speed as the focused laser beam must be scanned throughout the assay. In addition, the need for a translation stage for raster scan can increase the size, cost and complexity of the LFA reader.

SUMMARY

There is provided a system and method for photo-thermal imaging of lateral flow immunoassay devices.

In one aspect, a system for photo-thermal imaging of a lateral flow immunoassay (LFA) device is provided, the system comprising: an intensity modulated heat source directed at a surface of the LFA device to selectively excite chromophore particles of interest; a thermal capture device configured to capture thermal waves emitted from the surface of the LFA device as a radiometric signal; and a computing device, in communication with the thermal capture device, to receive the radiometric signal and execute lock-in demodulation to detect surface or subsurface inhomogeneities of the LFA device.

In a particular case, the chromophore particles are gold nanoparticles (GNPs).

In another case, lock-in demodulation comprises evaluating an alternating current (AC) portion of the radiometric signal.

In yet another case, lock-in demodulation comprises a determination of phase and amplitude with respect to a reference signal.

In yet another case, the system further comprises a controller configured to modulate the intensity of the heat source.

In yet another case, the intensity is modulated using an in-phase reference signal from a data acquisition device.

In yet another case, the computing device is in communication with the heat source and the computing device further executes depth profilometry by controlling the thermal diffusion length through changing the optical modulation frequency.

In yet another case, the heat source comprises a laser.

In yet another case, the thermal capture device has a spectral range in the range of 8 to 14 µm.

In yet another case, the thermal capture device is a thermal camera.

In yet another case, the heat source comprises a collimator, an optical diffuser, or both.

In yet another case, multiple laser wavelengths (serially or at once) are used to target multiple chromophores.

In yet another case, the infrared capture devices have different infrared ranges.

In yet another case, the infrared capture device comprises an array of infrared sensors.

In yet another case, the modulated heat source uses pulsed multiple frequency excitations to study a particular depth of LFA at once (i.e., scanning the thermal diffusion length).

In yet another case, matched filtering is used in place of lock-in demodulation.

In another aspect, a method for photo-thermal imaging of a lateral flow immunoassay (LFA) device is provided, the method comprising: thermally exciting, by intensity modulation, chromophore particles on or proximate a surface of the LFA device to produce emission of thermal waves; capturing the thermal waves as a radiometric signal; and performing lock-in demodulation on the radiometric signal to detect surface or subsurface inhomogeneities of the LFA device.

In one case, the chromophore particles are gold nanoparticles (GNPs).

In another case, lock-in demodulation comprises evaluating an alternating current (AC) portion of the radiometric signal.

In yet another case, lock-in demodulation comprises a determination of phase and amplitude images with respect to a reference signal.

In yet another case, the reference signal is an optical excitation modulation signal.

In yet another case, thermally exciting the chromophore particles comprises modulating an intensity of a heat source directed at the surface of the LFA device.

In yet another case, the intensity of the heat source is modulated using an in-phase reference signal.

In yet another case, performing depth profilometry comprises controlling a thermal diffusion length through an optical modulation frequency.

In yet another case, the emission of thermal waves is conducted at a plurality of wavelengths to target a plurality of chromophores of interest.

These and other embodiments are contemplated and described herein. It will be appreciated that the foregoing summary sets out representative aspects of various embodiments to assist skilled readers in understanding the following detailed description.

DESCRIPTION OF THE DRAWINGS

A greater understanding of the embodiments will be had with reference to the Figures, in which.

Figure 1:
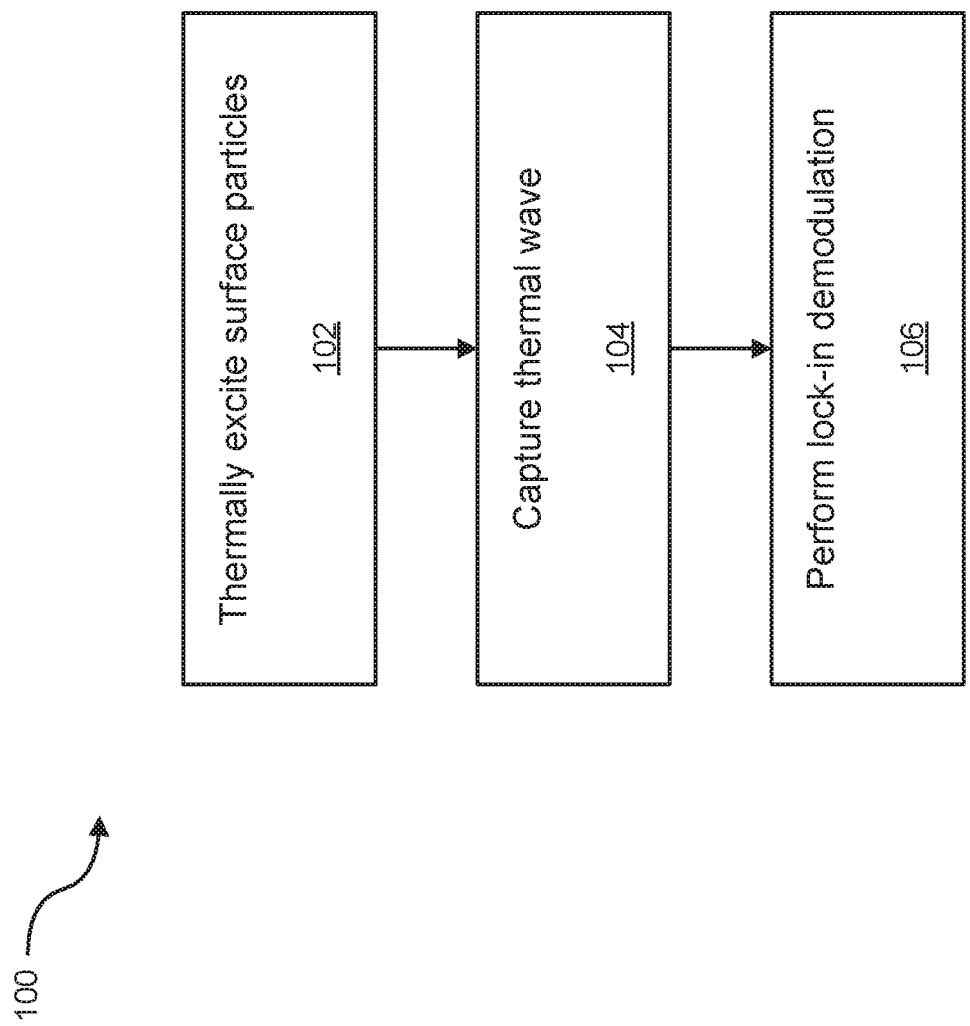
FIG. 1 shows an illustrative example of a method in accordance with an embodiment.

In the drawings, embodiments of the invention are illustrated by way of example. It is to be expressly understood that the description and drawings are only for the purpose of illustration and as an aid to understanding, and are not intended as a definition of the limits of the invention.

DETAILED DESCRIPTION

For simplicity and clarity of illustration, where considered appropriate, reference numerals may be repeated among the Figures to indicate corresponding or analogous elements. In addition, numerous specific details are set forth in order to provide a thorough understanding of the embodiments described herein. However, it will be understood by those of ordinary skill in the art that the embodiments described herein may be practised without these specific details. In other instances, well-known methods, procedures and components have not been described in detail so as not to obscure the embodiments described herein. Also, the description is not to be considered as limiting the scope of the embodiments described herein.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender. Further definitions for terms may be set out herein; these may apply to prior and subsequent instances of those terms, as will be understood from a reading of the present description.

Any module, unit, component, server, computer, terminal or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the device or accessible or connectable thereto. Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Any method, application or module herein described may be implemented using computer readable/executable instructions that may be stored or otherwise held by such computer readable media and executed by the one or more processors.

The present disclosure relates to a system and method for photo-thermal imaging of lateral flow immunoassay devices. Illustrative embodiments of the system and method will be described in detail with reference to the figures.

Conventional optical immunoassay readers, based on image acquisition and processing algorithms, typically rely on reflective signals, mostly in the visible spectral range, (i.e., color intensity) emanating from the surface of a lateral flow immunoassay (LFA) device. Thus, such readers can miss a large amount of signal from gold nanoparticles (GNP) trapped inside the bulk of the LFA nitrocellulose strips, possibly leading to suboptimal detection thresholds and sensitivities. The present embodiments can overcome this limitation by, for example, incorporating thermal waves that can penetrate deep into the LFA strips to collect diagnostic signals.

GNPs have traditionally been used due to their high affinity to antibodies, generation of an intense color for visualization, and nanoscale dimensions that enable easy migration through the LFA membrane. Due to their nanoscale dimensions, GNPs exhibit enhanced thermal properties that can act as a thermal contrast agent in Thermo-Photonic Lock-In imaging (TPLI). For the purposes of the present disclosure, GNPs are described as an example of a thermally reactive substrate and the disclosure applies equally to other suitable thermally reactive substrates.

TPLI is a technique that enables non-destructive testing and failure analysis of materials and devices. This technique incorporates intensity-modulated light to generate a thermal-wave field inside the material and uses the subsequent infrared emission of the thermal-wave field to detect material inhomogeneities. TPLI can have a superior detection threshold and sensitivity when compared with light scattering-based technologies.

In embodiments of the present disclosure, TPLI is used for detecting thermal infrared (Planck) radiation and using diffusive thermal waves as markers to gather information about subsurface material inhomogeneities.

Figure 2:
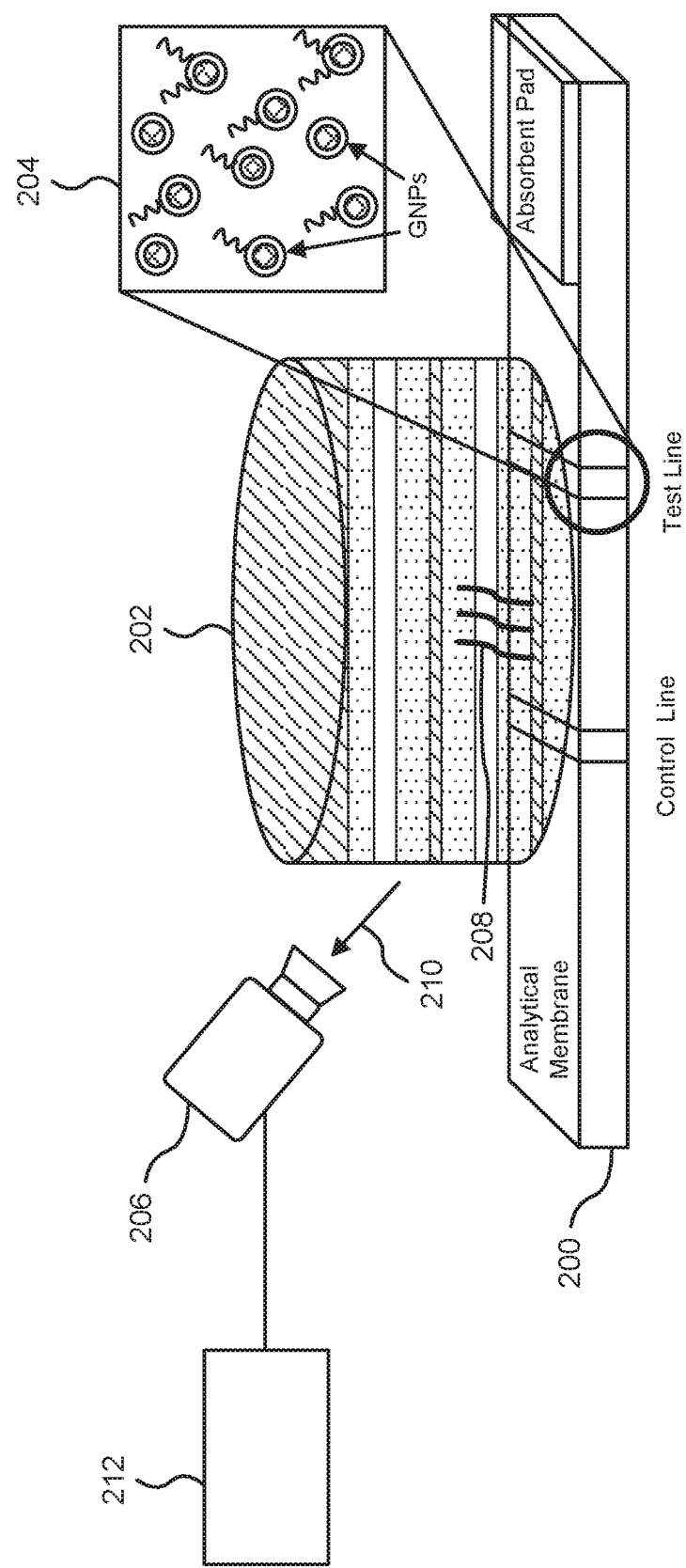
FIG. 2 shows an illustrative example of the method of FIG. 1.

FIG. 1 illustrates an embodiment of a method 100 for quantitative measurement of analyte concentrations in LFAs. FIG. 2 shows an example illustration of various aspects of the method 100. At block 102, a modulated heat source 202, such as a halogen lamp or a laser, is used to thermally excite chromophore(s) (in the illustrated example, gold nanoparticles (GNPs)) 204 of an LFA device 200. The wavelength for the modulated heat source 202 is tuned to the light absorption band of the chromophore of interest. Further, by varying the wavelength (or using multiple wavelengths at once with a plurality of modulated heat sources 202), it is possible to thermally excite several chromophores which, for example, could be used to measure various analytes on a single LFA. The varying of wavelengths may be accomplished with a single or a plurality of heat sources y using pulses of multiple frequency excitations to study the depth of the LFA at once.

Heat generated by the source 202 is selectively absorbed by the chromophore(s) of interest within the LFA device 200, generating thermal waves 208 that are transmitted to the surface of the LFA device through heat conduction 200. At block 104, the thermal waves 208 are captured via a thermal capture device (such as the illustrated thermal infrared camera 206) in the form of a depth-integrated radiometric signal 210. Alternatively, the thermal capture device may be a plurality of infrared cameras, each having different infrared wavelength ranges for targeting various chromophores of interest. Alternatively still, the thermal capture device may be an infrared sensor array used in place of the infrared camera.

In this embodiment, the thermal wave field 208 is altered as a result of selective light absorption and the consequent heat generation by chromophore(s) of interest compared to rest of the LFA device 200. The dissimilar heat generation leads to alteration of the local centroid of the thermal wave's 208 field, resulting in a phase shift in the thermal wave 208 as it reaches the surface and is captured by the thermal infrared camera through Planck radiation. This effect also results in a change in the amplitude of the radiometric signal 210 detected by the thermal infrared camera 206. Thus, interrogation of the phase and amplitude changes enables the measurement of the analyte at a determinable depth of the LFA substrate.

At block 106, lock-in demodulation is executed on a computing device 212, in communication with the thermal infrared camera 206, to evaluate the alternating current (AC) portion of the radiometric signal 210, which carries information about subsurface inhomogeneities. As such, lock-in demodulation of the radiometric signal 210 leads to a determination of phase and amplitude images with respect to a reference signal, which can be the optical excitation modulation signal produced by the heat source 202. Advantageously, thermo-photonic phase images are generally intrinsically emissivity normalized, which makes them insensitive to the variations in the optical power of the heat source 202 and/or surface conditions of the LFA device 200. This also improves the robustness of the quantitative comparison between different LFA devices. As an alternative to lock-in demodulation, matched filtering may be used.

Further, advantageously, method 100 allows for the performance of depth profilometry by controlling thermal diffusion length (eq. 1 below) through optical modulation frequency. The thermo-photonic phase images contain information from surface to a depth equal to thermal diffusion length (i.e., images are depth integrated). By changing the modulation frequency one can control the thermal diffusion length.

A lower modulation frequency of the heat source 202 that generates the thermal wave 208 leads to a deeper penetration of the thermal wave 208 into the LFA device 200. This penetration depth or thermal diffusion length is given by the equation:

$$\mu = \sqrt{\frac{\alpha}{\pi \cdot f_{lock-in}}}, \alpha = \frac{k}{\rho \cdot C_p} \quad (1)$$

where, $\mu$ is the thermal diffusion length (m), $\alpha$ is the thermal diffusivity (m$^2$/s) of the material, k (W/mK) is the thermal conductivity of the material, $\rho$ (kg/m$^3$) is the density of the material and $C_p$ (J/kgK) is the specific heat of the material at constant pressure. At low modulation frequencies, thermal waves face less spatial attenuation and therefore can effectively probe deeper into the material, which can yield superposed contributions from subsurface features within the long thermal diffusion length. For a given defect depth, increasing the modulation frequency can decrease the thermal diffusion length, which can lead to a lower effective detection depth and fading of the deeper features.

Figure 3:
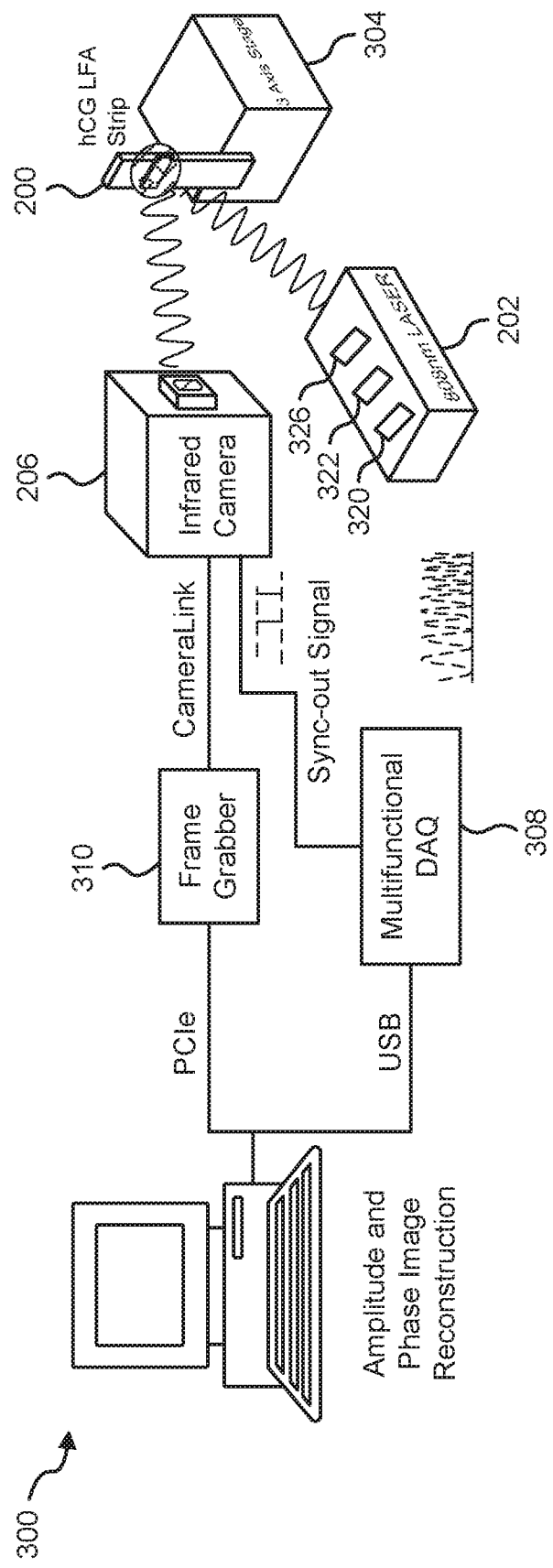
FIG. 3 shows an illustrative example of a system in accordance with an embodiment.
Figure 4:
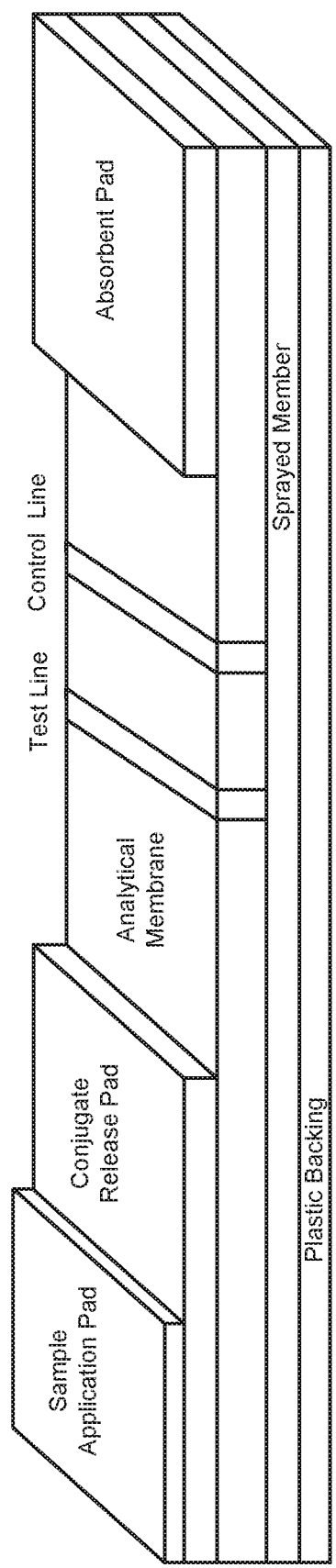
FIG. 4 shows an exemplary lateral flow immunoassay strip.

FIG. 3 illustrates a system 300 for quantitative measurement of analyte concentrations in LFAs, according to an embodiment.

In this embodiment, the system 300 includes the modulated heat source 202 and the LFA device 200; whereby the heat source 202 can be configured to thermally excite particles on the surface of the LFA device 200. In some cases, the LFA device 200 can be secured on a jig and mounted on a three-axis XYZ translation stage 304 in such a manner as to be in the incident path of the heat source 202. In a particular example, the heat source 202 can be a fiber-coupled (for example, having a core diameter=200 μm), continuous-wave near-infrared laser (for example, such as those produced by Jenoptik™) operating at, for example, 808 nm, with a modulation frequency that is automatically selected or selected by a user. The heat source could alternatively have a modulation pattern in form of a pulse or a multi-frequency waveform (e.g., a chirp).

In some cases, in order to have an illumination beam with uniform optical intensity over the interrogated area of the LFA device 200, a collimator 320 (for example, such as those produced by Thorlabs™ having model number F220SMA-780) and/or an optical diffuser 322 (for example, such as those produced by Thorlabs™ having model number ED1-C20-MD) can be coupled to the light source 202 in its incident path. In a particular case, a laser controller 326 (for example, such as those produced by Ostech™) coupled to the heat source 202 can be used to thermally stabilize the heat source 202 and to modulate its intensity. In some cases, the laser controller 326 can modulate the intensity of the heat source 202 using an in-phase reference signal from a multifunctional data acquisition device 308 coupled to the heat source 202.

The system 300 also includes the thermal infrared camera 206 positioned and configured to capture thermal waves emitted from the surface of the LFA device 200. In an example, the camera 206 can be a low-cost LWIR camera (for example, such as those produced by Xenics™) focused on the surface of the mounted LFA device 200. The camera can use a communication protocol (for example, CameraLink) to transmit readings to a frame grabber 210 or computing device 212. In such example, a spectral range of the camera 206 can be, for example, in the range of 8 to 14 μm, and have a maximum frame rate of, for example, 50 fps. Other examples of the spectral range of the camera 206 include 1-3 μm (SWIR) and 3-5 μm (MWI R).

In some cases, the camera 206 can have coupled thereto a focal-length objective lens (for example, such as those produced by Xenics™ having model number OPT-000179); for example, having a length of 18 mm. In some cases, the camera 206 can have an extension tube installed on the camera 206 to obtain a magnification of unity (1) from the interrogated surface of the LFA device 200. In some cases, a frame grabber 310 (for example, such as those produced by Euresys™ and called "Grablink Full") can be utilized to transfer acquired IR camera frames to a computer. In some cases, the multifunctional data acquisition device 308 (for example, such as those produced by National Instruments™ having model number USB-6363 BNC) can be used to synchronously gene, rate analog reference and trigger signals.

In an alternative embodiment, the modulated heat source may be disposed behind the LFA device and a thermal infrared camera can observe the IR emissions from in front of the LFA device. In this embodiment, the observation is being made in a "transmission mode" instead of a "reflection mode".

In another embodiment, excitation may be made by a non-optical source. For example, the source may be ultrasound to create heat at GNP sites.

The system 300 also includes the computing device 212 communicatively coupled directly or indirectly to the heat source 202 and thermal infrared camera 206. The computing device 212 can be configured to perform, for example, equipment control, data acquisition, and thermal data analysis. In a particular case, the computing device 212 executes lock-in demodulation to capture images from the camera 206 at a specified frame rate and record corresponding values of in-phase and quadrature signals, as well as a reference pulse train status (high or low). In some cases, captured image sequences can be analyzed and the beginning of a modulation cycle can be found using pulse train information. Reference signal values can be extracted to determine the weighted average of an image sequence corresponding to an integer multiple of lock-in modulation period using the instantaneous readings of the two reference signals. The weighted frames can be summed to obtain low-pass filtered in-phase)($S^0$ and quadrature ($S^{90}$) images. The amplitude and phase images can be determined by applying the following equation to each pixel:

$$A = \sqrt{(S^0)^2 + (S^{90})^2} \text{ and } \varphi = \arctan\left(\frac{S^{90}}{S_0}\right) \quad (2)$$

The applicant has determined through analysis that the presently disclosed system and method of quantitative measurement of analyte concentrations in LFAs can be significantly more accurate than visual or optical interpretation of LFA results. However, it will be understood that the experimental results provided herein are illustrative and to aid in the understanding for the reader only, and are not intended to promise any particular result.

In an example experimental verification, a visual analysis of LFA strips spiked with various hCG concentrations (0-16 mIU) by participants with no known visual disorders or impairments was conducted. It was determined that the limit of detection of LFA hCG strips visually with confidence (>90% accuracy) is only about 8 mIU, which is typically not very reliable for detecting lower concentrations of target biomolecules. A similar analysis was conducted by the Applicant using a commercial optical scanner. The optical scanner included a flat-bed surface onto which the LFA strips were loaded, a lamp located under the flat-bed surface to illuminate the strips, and a scanning head that included the CCD array, mirrors, filters and lenses for optical image acquisition. It was determined that the limit of detection of the optical scanner technology was about 2 mIU of spiked hCG hormone. This result can indicate that any lower concentration of antigen that occurs in early stages of pregnancy cannot be detected using the optical scanner technology.

Advantageously, the presently disclosed system and method of using TPLI to acquire quantified depth-integrated thermal information by considering contributions from GNPs located at various depths within the membrane can demonstrate superior performance. This performance is especially evident when compared to both human visual interpretation and optical strip readers that cannot detect the GNPs present in the bulk of the LFA. Specifically, experimentation conducted by the Applicant demonstrates that the TPLI approach of the present embodiments can be capable of statistically differentiating between zero and 0.2 mIU hCG concentrations. Such differentiation was shown to be typically not possible via optical or visual interpretation. Another advantage of the present embodiments is that, using TPLI, there is no physical contact by a user with the specimen during detection. Hence, it is possible to reduce contamination of the LFA and permit remote and high throughput interrogation of one more LFAs in a relatively short time.

It will be appreciated that the presently disclosed system may be applied to other devices beyond LFA. Whilst the application to LFA is based on the chromophore(s) of interest, it may be applied to other targets/analytes of interest in other applications. For example, the presently disclosed system may be applied to microfluidic chips, with suitable adjustments to the wavelengths of the heat source and the thermal capture device as appropriate for targets or analytes of interest in the microfluidic chips.

While illustrative embodiments have been described above by way of example, it will be appreciated that various changes and modifications may be made without departing from the scope of the invention, which is defined by the following claims.

We claim:

1. A system for photo-thermal imaging of a lateral flow immunoassay (LFA) device, the system comprising:
    an intensity modulated heat source directed at a surface of the LFA device to selectively excite chromophore particles of interest;
    a thermal capture device configured to capture thermal waves emitted from the surface of the LFA device as a radiometric signal; and
    a computing device, in communication with the thermal capture device, to receive the radiometric signal and execute lock-in demodulation to detect surface or subsurface inhomogeneities of the LFA device, the lock-in demodulation comprising evaluating an alternating current (AC) portion of the radiometric signal.

2. The system of claim 1, wherein the chromophore particles are gold nanoparticles (GNPs).

3. The system of claim 1, wherein the lock-in demodulation comprises a determination of phase and amplitude with respect to a reference signal.

4. The system of claim 1, wherein the intensity is modulated using an in-phase reference signal.

5. The system of claim 1, wherein the computing device is in communication with the intensity modulated heat source and the computing device further executes depth profilometry by controlling thermal diffusion length through changing optical modulation frequency.

6. The system of claim 1, wherein a heat source of the intensity modulated heat source comprises a laser.

7. The system of claim 1, wherein the thermal capture device has a spectral range in the range of 8 to 14 μm.

8. The system of claim 1, wherein the thermal capture device is a thermal camera.

9. The system of claim 1, wherein a collimator or an optical diffuser or both is disposed in an incident path of the intensity modulated heat source.

10. A method for photo-thermal imaging of a lateral flow immunoassay (LFA) device, the method comprising:
    thermally exciting, by intensity modulation, chromophore particles on or proximate a surface of the LFA device to produce emission of thermal waves;
    capturing the thermal waves as a radiometric signal; and
    performing lock-in demodulation on the radiometric signal to detect surface or subsurface inhomogeneities of the LFA device, the lock-in demodulation comprising evaluating an alternating current (AC) portion of the radiometric signal.

11. The method of claim 10, wherein the chromophore particles are gold nanoparticles (GNPs).

12. The method of claim 10, wherein the lock-in demodulation comprises a determination of phase and amplitude images with respect to a reference signal.

13. The method of claim 12, wherein the reference signal is an optical excitation modulation signal.

14. The method of claim 10, wherein thermally exciting the chromophore particles comprises modulating an intensity of a heat source directed at the surface of the LFA device.

15. The method of claim 14, wherein the intensity of the heat source is modulated using an in-phase reference signal.

16. The method of claim 10, further comprising performing depth profilometry comprising controlling a thermal diffusion length through an optical modulation frequency.

17. The method of claim 10, wherein the emission of thermal waves is conducted at a plurality of wavelengths to target a plurality of chromophores of interest.

18. The system of claim 1, wherein a heat source of the intensity modulated heat source comprises a halogen lamp.

* * * * *